US011672545B2

United States Patent
Gareiss et al.

(10) Patent No.: US 11,672,545 B2
(45) Date of Patent: Jun. 13, 2023

(54) ROTATIONALLY BALANCED SLOT PATTERN FOR FLEXIBLE SHAFTS

(71) Applicant: Avalign Technologies, Inc., Bannockburn, IL (US)

(72) Inventors: Warren Scott Gareiss, Columbia City, IN (US); Ryan Michael Ratkowski, Churubusco, IN (US)

(73) Assignee: AVALIGN TECHNOLOGIES, INC., Bannockburn, IL (US)

( * ) Notice: Subject to any disclaimer, the term of this patent is extended or adjusted under 35 U.S.C. 154(b) by 252 days.

(21) Appl. No.: 16/949,575

(22) Filed: Nov. 4, 2020

(65) Prior Publication Data

US 2022/0133335 A1 May 5, 2022

(51) Int. Cl.
*A61B 17/16* (2006.01)
*A61B 17/00* (2006.01)

(52) U.S. Cl.
CPC ............... *A61B 17/1631* (2013.01); *A61B 2017/00309* (2013.01)

(58) Field of Classification Search
CPC ... A61B 17/16; A61B 17/162; A61B 17/1631; A61B 17/8875; B23B 45/005; B25B 15/00; B25B 15/002
See application file for complete search history.

(56) References Cited

U.S. PATENT DOCUMENTS

| 6,053,922 | A  | * | 4/2000  | Krause  | A61B 17/164 606/180 |
|---|---|---|---|---|---|
| 6,258,093 | B1 |   | 7/2001  | Edwards et al. | |
| 6,447,518 | B1 | * | 9/2002  | Krause  | F16C 1/02 606/80 |
| 8,353,935 | B2 |   | 1/2013  | Krause  | |
| 9,138,263 | B2 |   | 9/2015  | Krause  | |
| 9,801,663 | B2 |   | 10/2017 | Krause  | |
| 9,808,867 | B2 | * | 11/2017 | Krause  | A61B 17/1631 |
| 10,569,396 | B2 | * | 2/2020 | Krause  | A61B 17/1631 |
| 10,842,535 | B2 | * | 11/2020 | Krause  | A61B 17/7029 |
| 2017/0189085 | A1 | * | 7/2017 | Krause  | A61B 17/7208 |
| 2018/0065235 | A1 | * | 3/2018 | Krause  | B23B 45/005 |
| 2020/0262038 | A1 | * | 8/2020 | Krause  | A61B 17/1631 |
| 2022/0133335 | A1 | * | 5/2022 | Gareiss | A61B 17/8875 606/80 |

OTHER PUBLICATIONS

International Patent Application No. PCT/US2021/034790; Int'l Search Report and the Written Opinion; dated Sep. 15, 2021; 12 pages.

* cited by examiner

*Primary Examiner* — Eric S Gibson
(74) *Attorney, Agent, or Firm* — BakerHostetler

(57) ABSTRACT

A flexible shaft includes a tubular body extending along a central longitudinal axis and having proximal and distal ends opposite one another. The flexible shaft also includes a slot defined by the tubular body and extending along a helical path around and along at least a portion of the body between the proximal and distal ends. The helical path extends around the portion of the body for a plurality of rotations. The slot defines at least two teeth adjacent one another along a direction parallel to the central axis. Each tooth of the two teeth has a feature. In some implementations, a line extending through center points of the features on the two teeth is angularly offset from the central longitudinal axis. In some implementations, a line parallel to the central longitudinal axis intersects a different point on each feature of the two teeth.

20 Claims, 14 Drawing Sheets

ROTATIONALLY BALANCED SLOT PATTERN FOR FLEXIBLE SHAFTS

TECHNICAL FIELD

This disclosure generally relates to devices and methods for rotating components via tools, and more particularly relates to a new design for a flexible shaft configured to transmit rotational forces from one end thereof to the other.

BACKGROUND

A principle application of a flexible shaft is to transmit rotary motion and power in a curvilinear manner. Flexible shafts are commonly used in situations where a straight, rigid shaft cannot reach a target location. A specific exemplary application of flexible shafts is for use with medullary canal reamers, which are used to enlarge the medullary canal of bones for receiving prosthetic components or fixation devices and to otherwise provide access to the medullary canal. Because the shafts of long bones are generally bent or curved along their longitudinal axes, utilizing a straight and rigid shaft to perform the desired tasks within the canal would be difficult and can result in decreased precision.

For example, during the reaming process, a straight shaft will not remove the desired amount of bone at the needed portions within the bone, resulting in a non-uniform internal diameter. Rigid shafts also increase risk of jamming within the canal, resulting in damage to the bone or excessive removal of the bone. As such, instead of straight, rigid shafts, it can be advantageous to utilize flexible screw shafts that can bend to follow the curved pathway while transmitting the necessary torque required to perform the desired actions within the canal. In view of the above, medullary reamers are designed to be flexible.

However, there are shortcomings with conventional flexible shafts. Specifically, existing flexible shafts often result in unbalanced bending stiffness along the length of the shaft, which negatively affects precision and accuracy of using the tool. The foregoing deficiencies are addressed by various embodiments of flexible shafts and tools utilizing flexible shafts.

SUMMARY

According to an embodiment of the disclosure, a flexible shaft includes a tubular body extending along a central longitudinal axis, the tubular body having a proximal end and a distal end opposite the proximal end. The flexible shaft also includes a slot defined by the tubular body and extending along a helical path around and along at least a portion of the tubular body between the proximal end and the distal end. The helical path extends around the portion of the tubular body for a plurality of rotations. The slot defines at least two teeth adjacent one another along a direction parallel to the central axis. Each tooth of the two teeth has a feature. A line extending through center points of the features on the two teeth is angularly offset from the central longitudinal axis.

In some embodiments, a flexible shaft includes a tubular body extending along a central longitudinal axis, the tubular body having a proximal end and a distal end opposite the proximal end. The flexible shaft also includes a slot defined by the tubular body and extending along a helical path around and along at least a portion of the tubular body between the proximal end and the distal end. The helical path extends around the portion of the tubular body for a plurality of rotations. The slot defines at least two teeth adjacent one another along a direction parallel to the central longitudinal axis. Each tooth of the two teeth has a feature. A line parallel to the central longitudinal axis intersects a different point on each feature of the two teeth.

In some embodiments, a modular flexible shaft includes a tubular body having a proximal end and a distal end opposite the proximal end. The tubular body extends along a central longitudinal axis between the proximal end and the distal end. The modular flexible shaft further includes a slot extending along a helical path around and along at least a portion of the tubular body between the proximal end and the distal end, and a modular connection disposed on the distal end, the modular connection being configured to releasably couple to a modular component. The helical path extends around the portion of the tubular body for a plurality of rotations. The slot defines at least two teeth adjacent one another along a direction parallel to the central longitudinal axis, each tooth of the two teeth having a feature. A line extending through center points of the features on the two teeth is angularly offset from the central longitudinal axis.

BRIEF DESCRIPTION OF THE DRAWINGS

The present application is further understood when read in conjunction with the appended drawings. For the purpose of illustrating the subject matter, there are shown in the drawings exemplary aspects of the subject matter; however, the presently disclosed subject matter is not limited to the specific methods, devices, and systems disclosed. In the drawings.

Aspects of the disclosure will now be described in detail with reference to the drawings, wherein like reference numbers refer to like elements throughout, unless specified otherwise.

DETAILED DESCRIPTION OF ILLUSTRATIVE EMBODIMENTS

Embodiments of tools are disclosed throughout this application and include flexible shaft components that allow for the curving of at least a portion of the tool relative to the longitudinal axis of the tool. The flexible shafts disclosed herein can be manufactured from a rigid material with a rigid first end capable of receiving an instrument to impart rotary motion thereon (e.g. a screwdriver handle or a drill chuck) and a rigid second end dimensioned to contact a device to rotated (e.g. a reamer or a screw). The flexible shaft may be hollow inside between the first and second ends and may define a lumen therein. A central longitudinal axis extends along the centerline of the flexible shaft between the first and second ends. At least a portion of the flexible shaft is configured to be bent. Rotational force can be imparted at the first end and transferred to the second end along the flexible shaft, including along the flexible portion of the shaft. Structural and functional details will be explained below with reference to exemplary illustrations.

Figure 1:
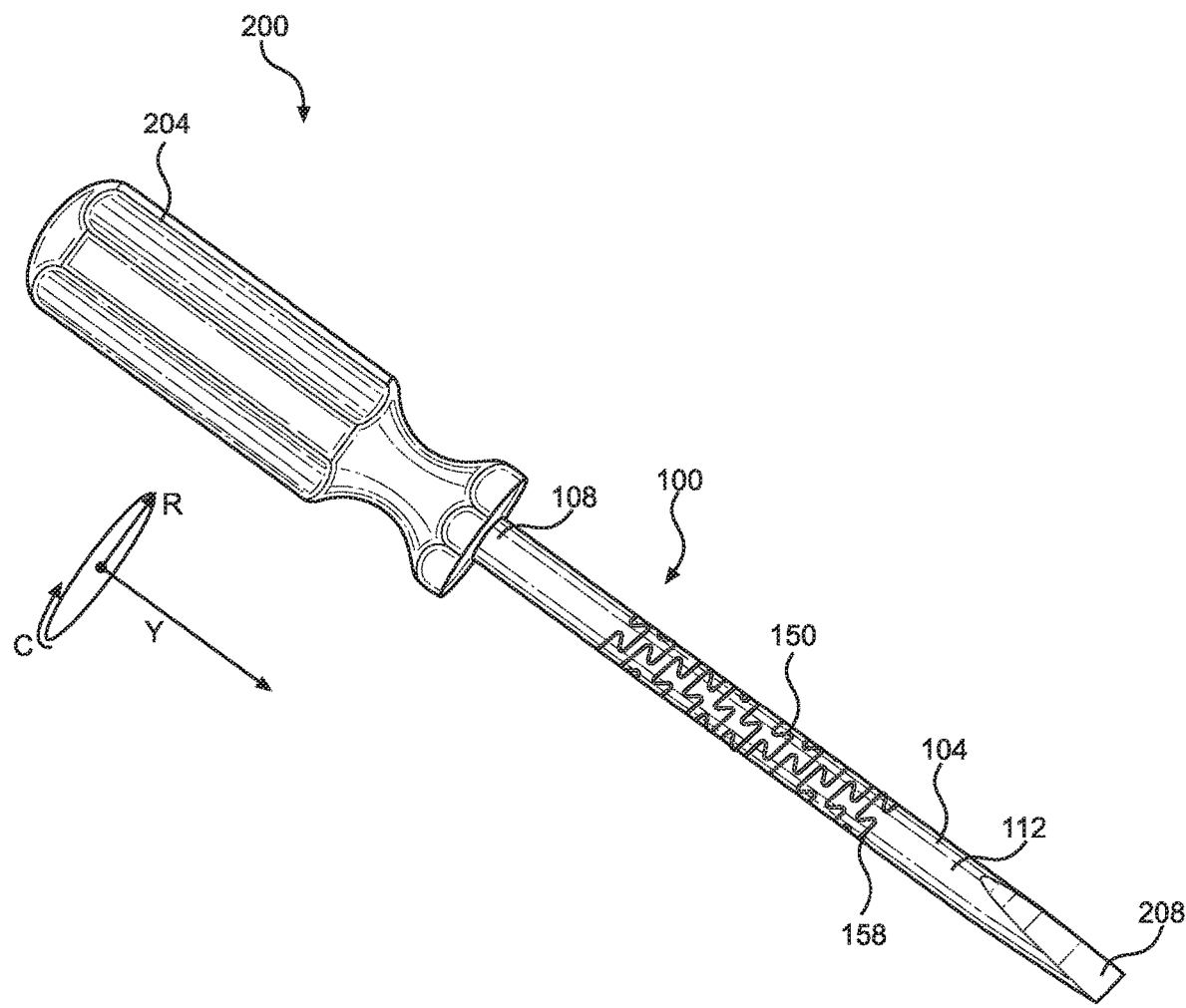
FIG. 1 illustrates a perspective view of a screwdriver having a flexible shaft according to an aspect of the disclosure.
Figure 2:
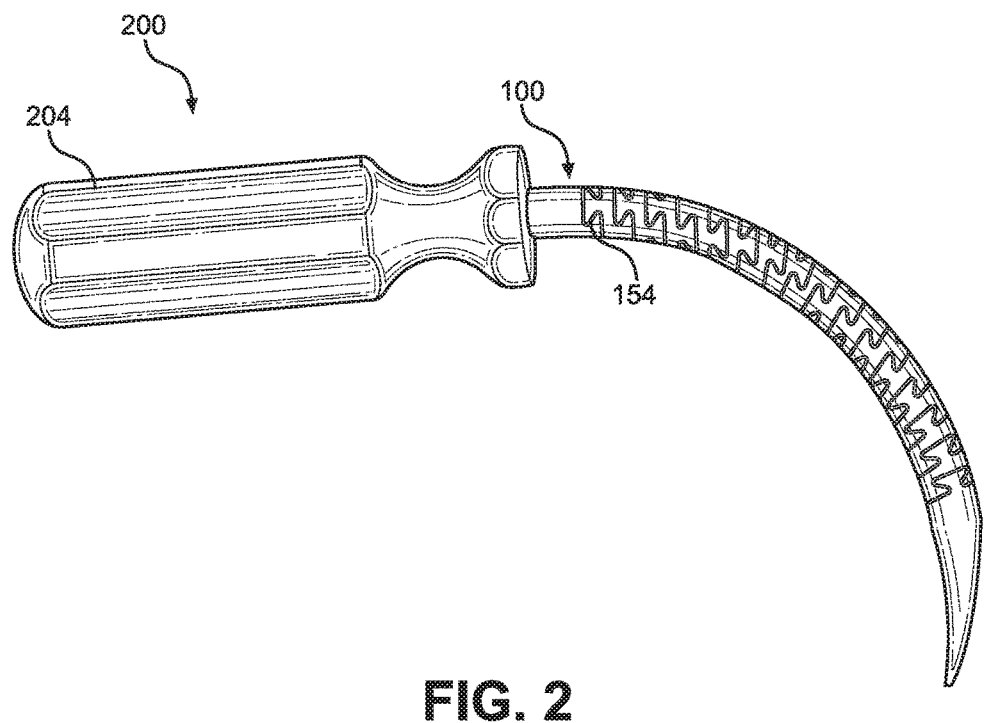
FIG. 2 illustrates the screwdriver of FIG. 1 with the shaft shown bent.
Figure 13:
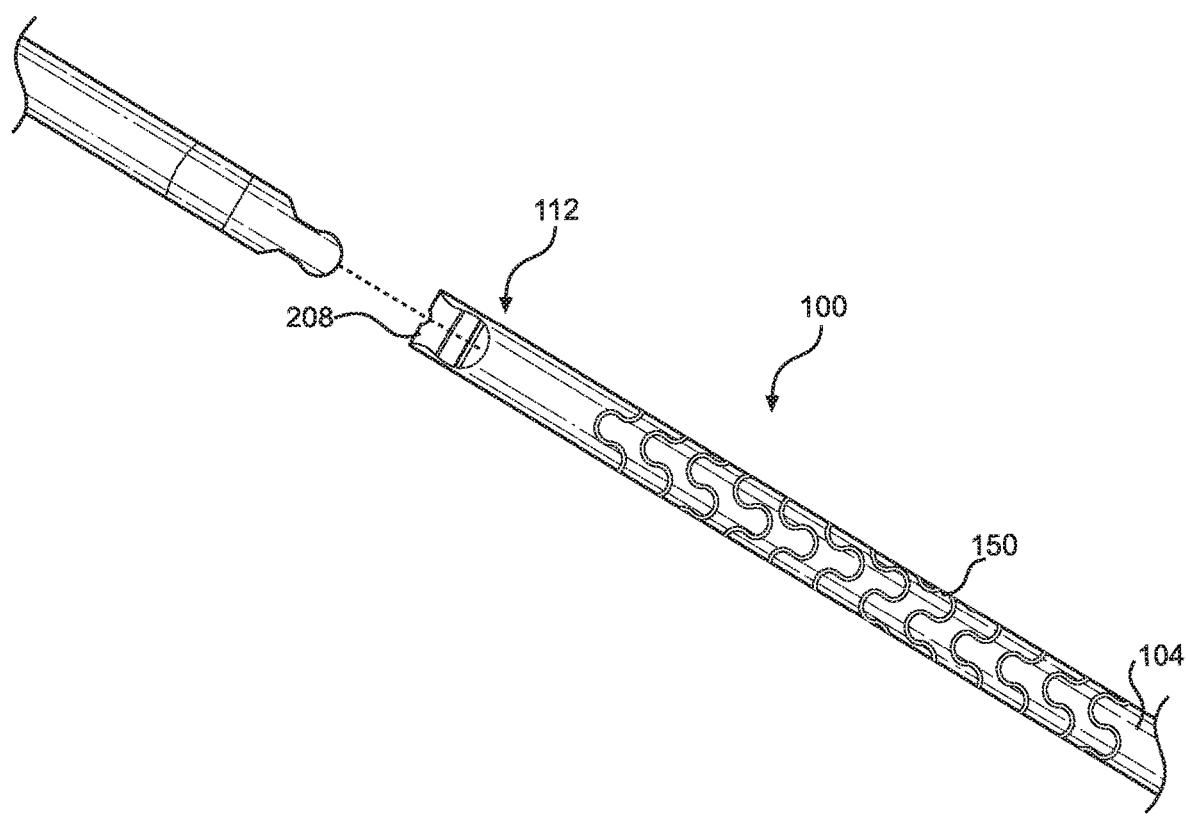
FIG. 13 illustrates a cross-sectional side view of a modular flexible shaft and a modular component according to an aspect of the disclosure.

Referring to FIGS. 1 and 2, an exemplary embodiment of a screwdriver 200 is depicted having a flexible shaft 100. The flexible shaft 100 includes a tubular body 104 having a proximal end 108 and a distal end 112 opposite the first end. As shown in the depicted embodiment, the flexible shaft 100 may be coupled to a handle 204 at the proximal end 108. The shaft 100 may be permanently or releasably coupled to the handle 204. In operation, a user may grip the handle 204 and translate or rotate the screwdriver 200. The distal end 112 of the shaft 100 may include a desired tool engagement tip 208. FIGS. 1 and 2 depict the tool engagement tip 208 and the shaft 100 as a monolithic piece, but it will be understood that the tool engagement tip 208 may alternatively be coupled (either permanently or removably) to the distal end 112 of the shaft 100. The tool engagement tip 208 may be a screwdriver tip, such as a flat slot, Phillips, Torx, spline, spanner, hex, square, or another suitable screw drive configuration. The tool engagement tip 208 may be a coupling mechanism configured to releasably couple to an modular component. In some embodiments, the tool engagement tip 208 may include, or may be coupled to, a drive bit, a reamer bit, or another rotating end effector tool. The tool engagement tip 208 may be configured to interface, in a rotating manner, with another device or with a target substrate (e.g. with bone). In some embodiments, the flexible shaft 100 may be modular so as to be configured to releasably engage with one or more separate components at the proximal end 108 and/or at the distal end 112. In some embodiments, the tool engagement tip 208 may be a modular connector that is configured to receive an external component therein. As shown in FIG. 13, a shaft 100 can include a tool engagement tip 208 configured to receive a modular component 210 therein. The tool engagement tip 208 shown in FIG. 13 may be a receptacle that is configured to receive and engage with a protrusion on the modular component 210. In the depicted example of FIG. 13, the modular component 210 may include a bulb-shaped protrusion, and the receptacle defined by the engagement tip 208 may have a concave shape configured to complement the bulb shape of the modular component 210. It will be appreciated that the depicted arrangement can be reversed, such that the protrusion is on the tool engagement tip 208 while the receptacle is on the modular component 210. It will be further understood that the particular shape of the modular component 210 and the engagement tip 208 can be any other suitable shape and is not limited to the bulb and receptacle for the bulb as shown in FIG. 13. In other embodiments, the engagement may between a trapezoidal protrusion on one of the modular component 210 and the engagement tip 208 and a receptacle configured to receive the trapezoidal protrusion, the receptacle being on the other of the modular component 210 and the engagement tip 208. In other embodiments, the engagement may be between a suitable connection interface disposed on one of the modular component 210 and the engagement tip 208 and between a complementary connection interface on the other of the modular component 210 and the engagement tip 208, such as, but not limited to, hex, square, AO, Hudson, or another suitable connection interface. In such arrangements as described above, any rotational, compressive, or tensile forces exerted onto the shaft 100 may be transferred, via the tool engagement tip 208, to the connected modular component 210.

The flexible shaft 100 includes at least one portion of the tubular body 104 that is configured to be bent (see FIG. 2). The range of curvature will depend on the length and pattern of the tubular body 104, as well be described in detail below.

Figure 3:
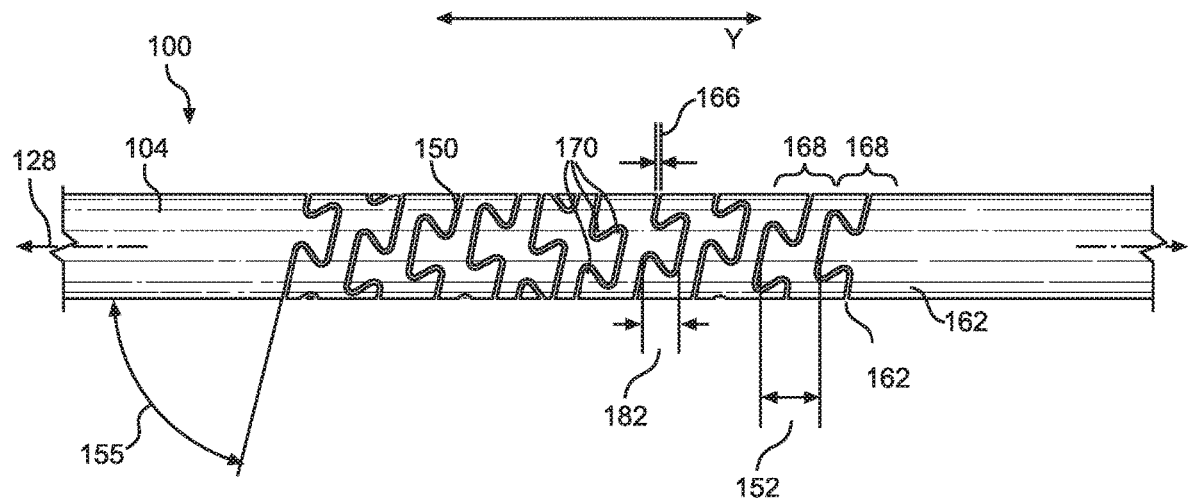
FIG. 3 illustrates a side perspective view of a portion of a flexible shaft according to an aspect of the disclosure.
Figure 4:
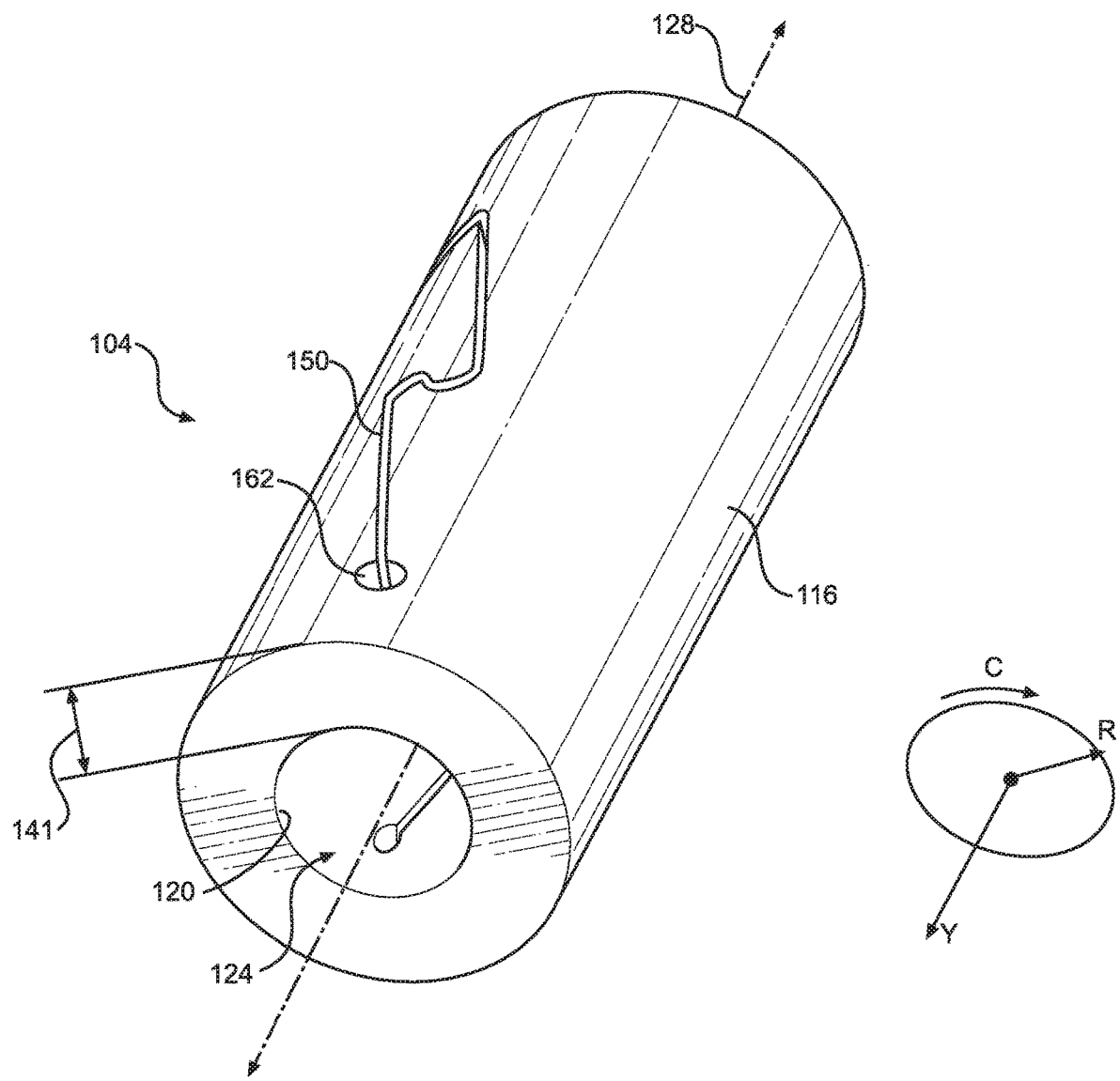
FIG. 4 illustrates an angled perspective view of another portion of a flexible shaft according to an aspect of the disclosure.

Referring to FIGS. 3 and 4, an exemplary flexible shaft 100 is depicted. The shaft 100 includes a tubular body 104 extending between a proximal end 108 and a distal end 112 along a longitudinal direction y. The tubular body 104 may be substantially cylindrical, having a curved outer surface 116 extending between the proximal and distal ends 108, 112. A central longitudinal axis 128 extends along the length of the tubular body 104 between the proximal end 108 and the distal end 112. The central longitudinal axis 128 is parallel to the longitudinal direction y. The central longitudinal axis 128 is defined along the geometric centerline of the tubular body 104.

The tubular body 104 may be hollow and have an inner surface 120 spaced radially away from the outer surface 116 along the radial direction r (see FIG. 4). The radial direction r is perpendicular to the longitudinal direction y. The inner surface defines a lumen 124 extending through the tubular body 104 between the proximal and distal ends 108, 112. The tubular body 104 has a thickness 141 being measured between the outer surface 116 and the inner surface 120 along the radial direction r perpendicular to the central axis 128. In some examples, the thickness 141 of the tubular body 104 may be between about 0 and about 0.14 inches.

A slot 150 is defined on the tubular body 104 between the proximal end 108 and the distal end 112 of the tubular body 104. The slot 150 has a first end 154 (see FIG. 2) and a second end 158 (see FIG. 1). The slot 150 extends circumferentially around and along at least part of the length of the tubular body 104 in a helical path. The first end 154 of the slot 150 is disposed on the tubular body 104 between the proximal end 108 of the tubular body 104 and the second end 158 of the slot 150. The second end 158 of the slot 150 is disposed on the tubular body 104 between the first end 154 and the distal end 112 of the tubular body 104. The central longitudinal axis 128 extends through the center of the helical path of the slot 150, and the slot 150 wraps around the central axis 128 as it helically winds along the tubular body 104 in the longitudinal direction y. The helical path may extend around the tubular body 104 for a plurality of rotations. In some embodiments, the slot 150 follows a cylindrical helical pathway and has substantially equal pitch along the length of the slot 150 between the first and second ends 154, 158. In some alternative embodiments, the pitch may vary along the slot 150.

The slot 150 may extend through the midpoint of the tubular body 104 measured between the proximal and distal ends 108, 112 along the central longitudinal axis 128. In such a configuration, the tubular body 104 may bend about its midpoint. In some examples, the slot 150 may be disposed between the proximal end 108 and the midpoint of the tubular body 104. In other examples, the slot 150 may be disposed between the midpoint of the tubular body 104 and the distal end 112.

The slot 150 may extend through the tubular body 104 in a radial direction between the outer surface 116 and the inner surface 120. The first end 154 of the slot 150 may include a stress relief opening 162. Additionally or alternatively, the second end 158 of the slot 150 may include a stress relief opening 162. The stress relief openings 162 are throughbores that may have a circular cross-section (when viewed along the radial direction r). It will be appreciated that the stress relief opening 162 may be another suitable shape, such as, an oval. The presence of the stress relief opening 162 at one or both ends 154, 158 of the slot 150 helps to reduce the stress concentration applied to the tubular body 104 to reduce the risk of the tubular body 104 cracking or breaking under pressure.

The slot 150 may be partially or entirely filled with a resilient material. The resilient material can be an elastomer compound, and can include, for example, urethane and silicone. The resilient material may additionally, or alternatively, be added to one or more of the lumen 124, outer surface 116, and inner surface 120.

The slot 150 may be formed in or on the tubular body 104 at an angle normal to the shaft 100 using a computer controlled cutting technique, such as laser cutting, water jet cutting, milling, or other means. In some examples, the slot 150 may be cut at an angle to the normal so as to provide an undercut slot having a preferred angle from the normal, relative to the shaft 100.

The slot 150 may define a variety of suitable patterns. In some embodiments, the slot 150 may have a serpentine or sinusoidal pattern. The sinusoidal pattern may define a plurality of interlocking teeth 170 along the length of the slot 150. Adjacent teeth 170 are separated by the slot 150. The slot 150 defines a width 166 that is sufficient to form an unbound joint between adjacent teeth 170 so as to permit limited movement in any direction between the adjacent teeth 170. This allows for limited flexibility in all directions upon application of tensile, compressive, and/or torsion forces to the shaft 100. When transferring rotary motion, adjacent teeth 170 interlock with each other regardless of whether the shaft 100 is straight or bent.

The width 166 of the slot 150 can be consistent or can vary along the length of the tubular body 104 to provide the varied flexibility. In some exemplary embodiments, the width 166 of the slot 150 may be between about 0.005 inches to about 0.25 inches. In some preferred embodiments, the width 166 of the slot 150 may be between about 0.005 inches to about 0.075 inches. In further preferred embodiments, the width 166 may be between about 0.01 inches to about 0.05 inches. The width 166 of the slot 150 may be between about 2.5% to about 20% of the diameter of the tubular body 104. The width 166 may contribute to the flexibility of the shaft 100, and the width 166 may be changed to arrive at the desired flexibility.

In some embodiments, the tubular body 104 may define a plurality of slots 150. The plurality of slots 150 may be arranged in series, with one of the plurality of slots 150 following another of the plurality of slots 150 along the tubular body 104 (see exemplary embodiment of FIG. 12). In some embodiments, two or more slots 150 may overlap with one another (not shown), such that at least a portion of each of the two or more slots 150 are defined on the same portion of the tubular body 104. The plurality of slots 150 may have different shapes and dimensions, or, alternatively, all of the plurality of slots 150 may have the same shape and/or dimensions.

Figure 5A:
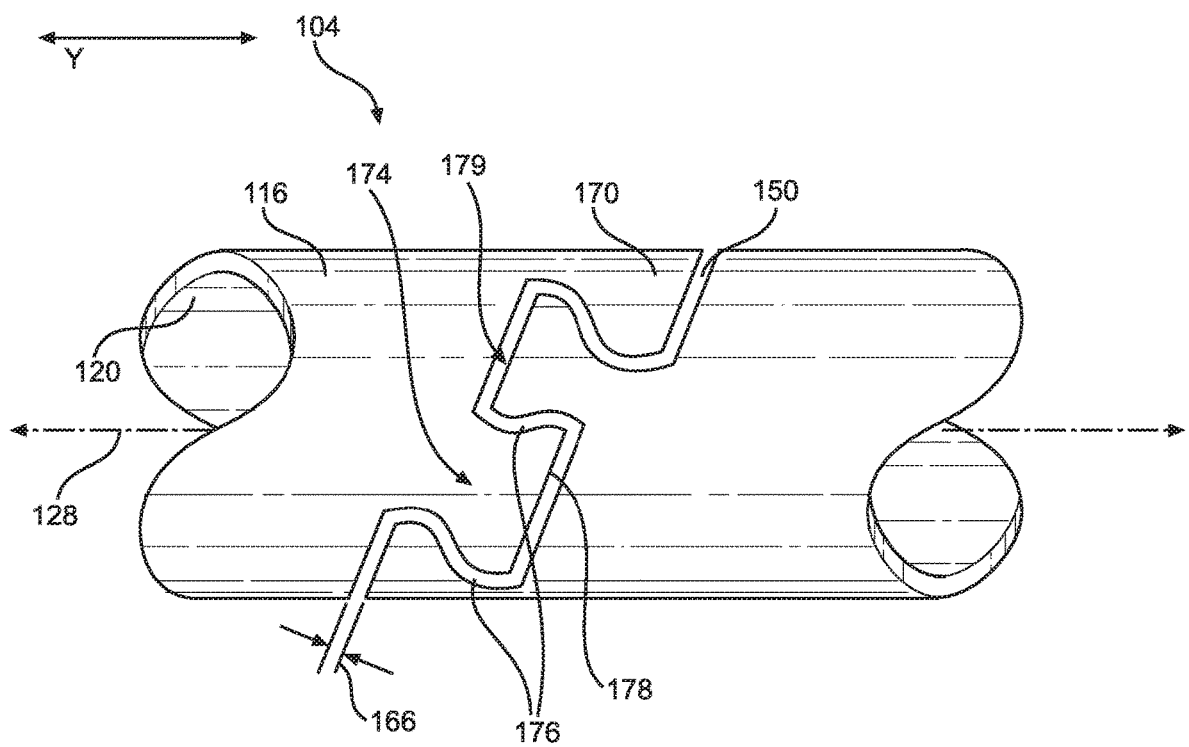
FIG. 5A illustrates a side perspective view of another portion of a flexible shaft according to an aspect of the disclosure.
Figure 5B:
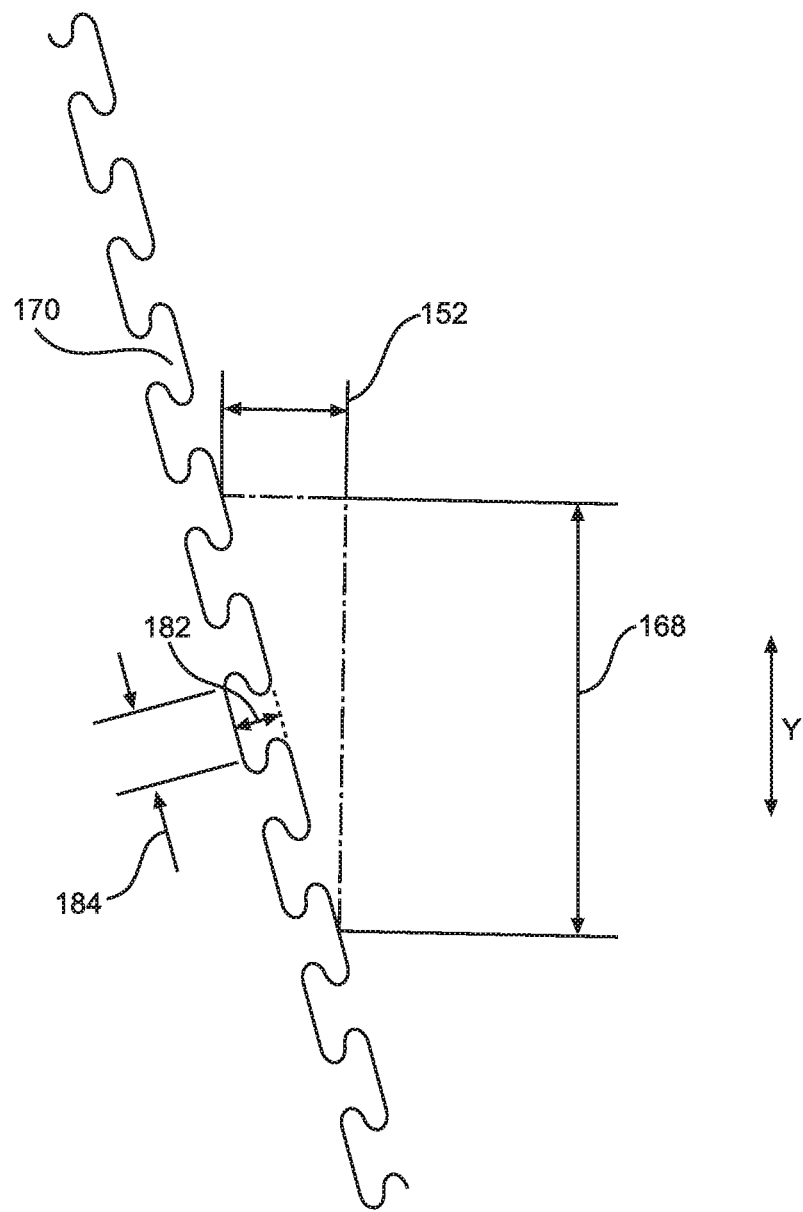
FIG. 5B illustrates a helical slot according to an aspect of the disclosure.

Each tooth 170 includes a base 174 and a crown 178. Two walls 176 extend between the base 174 and the crown 178. The crown 178 has a center point 179 located on the crown 178 equidistantly from each of the two walls 176. Each tooth 170 may include at least one feature thereon, such as the crown 178 or the center point 179 of the crown 178. Referring to FIGS. 1-5, the teeth 170 may be dovetail-shaped, wherein the base 174 is narrower than the crown 178. In some embodiments, the crown 178 may be substantially flat and extend along a straight line between the two walls 176. In alternative embodiments, the crown 178 may be curved between the two walls 176 (see FIGS. 6A, 6B, 6C, 10, and 11). As shown in FIG. 5B, each tooth 170 has a height 182 measured between the base 174 and the crown 178. The height may be measured in a direction orthogonal to the helical path of the slot 150. Each tooth 170 has a width 184 measured between the two walls 176. The width 184 may be measured at the widest part of the tooth 170. In depicted examples where the teeth 170 are dovetail-shaped, the widest portion of each tooth 170 is adjacent the crown 178.

A rotational force can be applied along the rotational direction c (see FIG. 1). The rotational direction c extends circumferentially around the longitudinal direction y. In operation, rotational force may be applied in a first rotational direction (e.g. counterclockwise) (see FIG. 6B) or in a second rotational direction opposite the first rotational direction 10a (e.g. clockwise) (see FIG. 6C) as will be discussed in detail below. The first and second rotational directions are applied circumferentially around the central axis 128. If the shaft 100 is engaged with the tool, fastener, or another component at the distal end 112 of the tubular body 104, a responsive, normal force is applied to the shaft 100 in response to the rotational force. When this happens, at least some of the teeth 170 move across the width 166 of the slot 150 towards adjacent teeth 170 and contact the adjacent teeth 170. When the teeth 170 contact each other, the width 166 of the slot 150 at the point of contact of the teeth 170 is zero. The instrument used to initiate rotary motion can be manual, such as a handle, or powered. The tool can be, among other tools, a reamer, drive bit, screwdriver or extension bar.

Figure 6A:
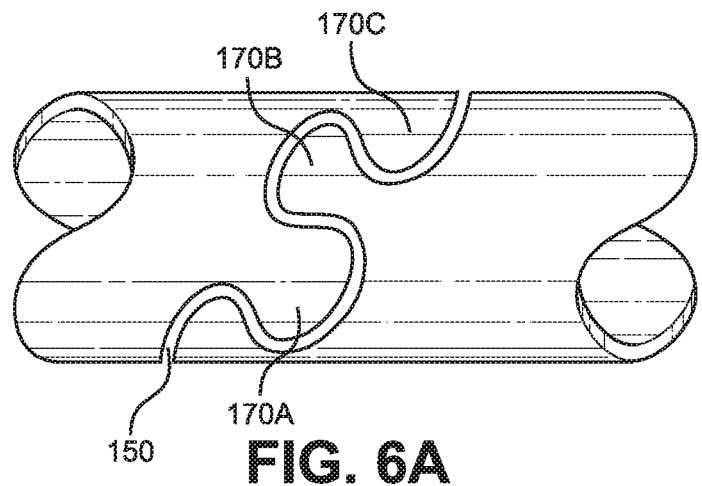
FIG. 6A illustrates another side perspective view of a portion of the flexible shaft according to an aspect of the disclosure, the shaft not shown in torsion.

FIGS. 6A-6D depict various possible configurations of the shaft 100. For ease of description, three exemplary adjacent teeth 170 will be arbitrarily numbered and referred to as a first tooth 170a, a second tooth 170b, and a third tooth 170c. For purposes of this disclosure, the first, second, and third teeth 170a-c can be substantially the same. The first tooth 170a is separated from the second tooth 170b by the slot 150. Similarly, the third tooth 170c is separated from the second tooth 170b by the slot 150. FIG. 6A depicts a portion of the shaft 100 where the shaft 100 is not in torsion (i.e. there are no rotational forces applied at one end of the shaft and normal, responsive forces applied at the other end of the shaft). As shown in FIG. 6A, adjacent teeth 170 are spaced apart from each other by the slot 150. The adjacent teeth 170 do not contact each other in this configuration.

Figure 6B:
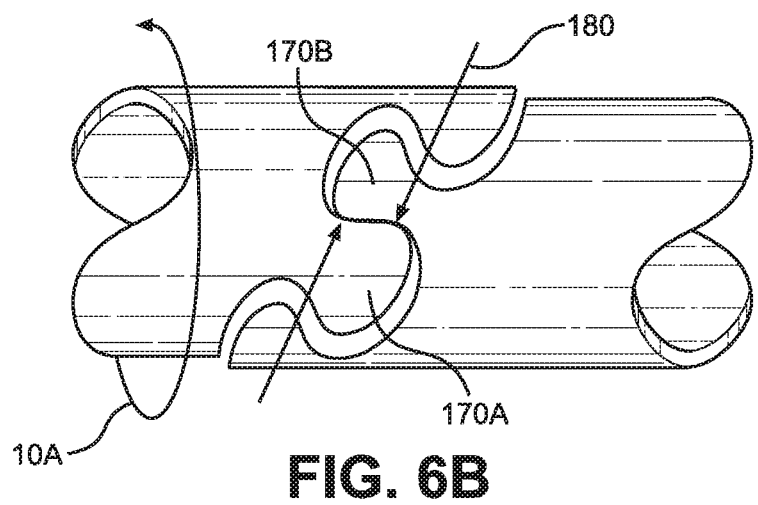
FIG. 6B illustrates a side perspective view of the portion of the shaft in FIG. 6A being rotated in a first rotational direction.

FIG. 6B depicts the shaft 100 shown in FIG. 6A receiving a rotational force in a first rotational direction 10a as depicted by the arrow. The rotational force causes adjacent teeth 170 to contact one another. As shown in FIG. 6B, the first tooth 170a is moved across the width 166 of the slot 150 and contacts the second tooth 170b at a contact point 180. The contact point 180 may be between a wall 176 on the first tooth 170a and an adjacent wall 176 on the second tooth 17b. In some aspects, the contact point 180 may be between the crown 178 of one of the first and second teeth 170a, 170b and a wall 176 on the other of the first and second teeth 170a, 170b.

Figure 6C:
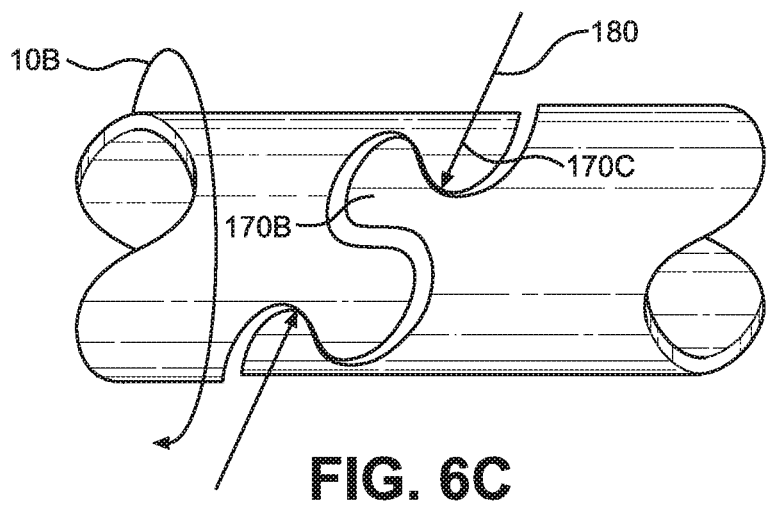
FIG. 6C illustrates a side perspective view of the portion of the shaft in FIG. 6A being rotated in a second rotational direction.

Referring to FIG. 6C, the shaft 100 is shown receiving a rotational force in a second rotational direction 10b that is opposite the first rotational direction 10a shown in FIG. 6B. Here, the third tooth 170c is moved across the width 166 of the slot 150 and contacts the second tooth 170b at another contact point 180.

Figure 6D:
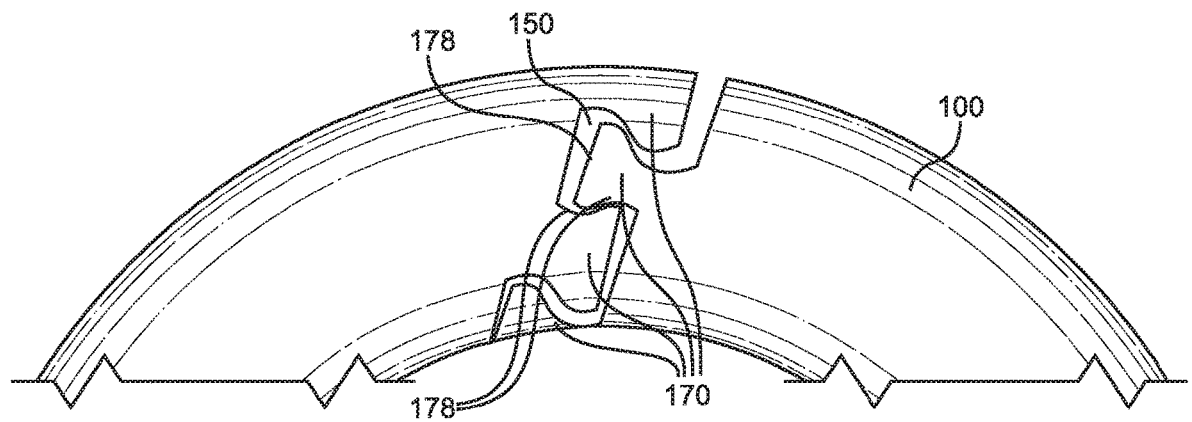
FIG. 6D illustrates a side perspective view of the portion of the shaft in FIG. 6A being bent.
Figure 6E:
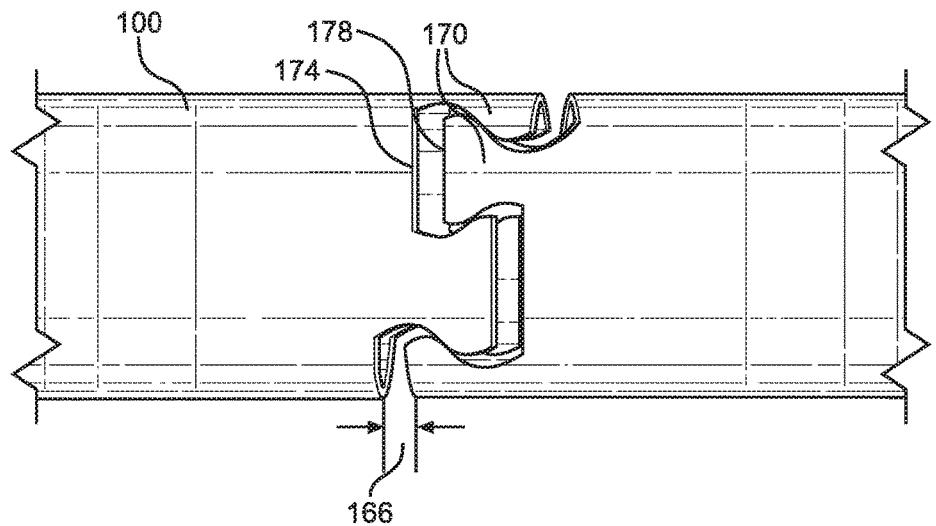
FIG. 6E illustrates a top perspective view of the portion of the shaft in FIG. 6D.
Figure 6F:
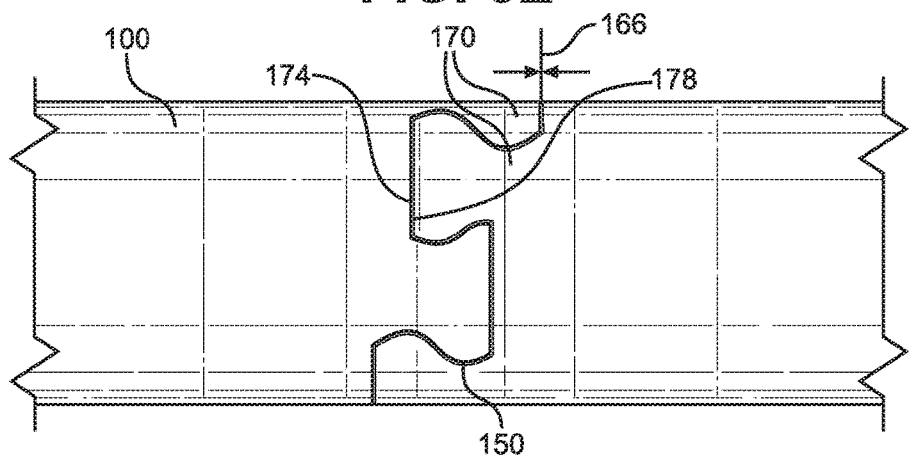
FIG. 6F illustrates a bottom perspective view of the portion of the shaft in FIG. 6D.

Referring to FIGS. 6D-6F, the shaft 100 is shown receiving a longitudinal force to bend the shaft 100. The amount of bending and the radius of curvature of the bend along the shaft 100 can be determined by the forces applied to the shaft 100 to cause the bending, as well as the definition of the slot 150 and the teeth 170 arranged relative to each other along the slot 150. As the shaft 100 is bent, the side of the shaft 100 on the outside of the bend is in tension, while the opposite side of the shaft 100 that is on the inside of the bend is in compression. As shown in FIG. 6E, teeth 170 disposed on the outside of the bend are spaced farther apart from each other across the slot 150 than the teeth 170 disposed on the inside of the bend shown in FIG. 6F. Specifically, as the surface of the shaft 100 on the outside of the bend is put in tension during bending, teeth 170 that engage with each other across the slot 150 move away from each other, thus increasing the size of the slot 150 between the engaged teeth 170. It should be noted that the teeth 170 are still engaged with each other, as shown in FIG. 6E, and the teeth 170 do not disengage from each other entirely during their movement away from each other. This continued engagement prevents separation of teeth 170 and breakage of the shaft 100 during bending. When the teeth 170 opposite each other across the slot 150 are spaced at a maximum distance while still being engage with one another, the width 166 of the slot 150 is at its intended maximum value. The engagement of the teeth 170 serves as a physical inhibitor to prevent further bending of the shaft 100. On the opposite side of the shaft 100, at the inside of the bend, the teeth 170 are moved towards each other across the slot 150, which decreases the size of the slot 150. When the crown 178 of one of the teeth 170 contacts a base 174 of another tooth 170 across the slot 150, the slot 150 between these two teeth 170 may have a width 166 of zero. When the width 166 of the slot 150 is zero at the inside of the curve during bending of the shaft 100, the shaft 100 is bent to the smallest radius of curvature that its structure is designed to permit.

It will be understood that as the rotational force is continuously applied in either the first or second directions 10a, 10b, more of the plurality of teeth 170 will move and contact adjacent teeth 170 in the manner described above.

The parameters of the slot 150 and the dimensions of the teeth 170 can affect how the shaft 100 transmits rotational forces along the length of the tubular body 104 from the proximal end 108 (e.g. the end receiving the rotational force) to the distal end 112 (e.g. the end transmitting the rotational force to a tool, fastener, or other component). Referring again to FIGS. 3-5A, the helical sinusoidal slot 150 rotates around the tubular body 104 (and around the central longitudinal axis 128) and along the length of the tubular body 104 (in a direction parallel to the central axis 128) along a helical path. For purposes of this disclosure, a single "rotation" 168 of the slot 150 along the helix corresponds to the length of a portion of the slot 150 that travels from a single point on the tubular body 104 around the tubular body 104 for 360 degrees. FIG. 5B depicts the helical slot 150 if it were unraveled and laid first end 154 to second end 158. FIG. 5B shows a single rotation 168, which corresponds to the circumferential distance that the slot 150 travels around the tubular body 104 for about 360 degrees.

The "pitch" of the helix is the linear measurement between the same points on two consecutive adjacent rotations of the helix. The pitch can be measured along a direction parallel to the central axis 128. FIG. 3 depicts a pitch 152 of the helical slot 150 measured from approximately the center of the crown 178 of a tooth 170 on one rotation 168 to approximately the center of the crown 178 of a tooth 170 on the adjacent rotation 168. It will be understood that the pitch 152 may be measured between any two same points on adjacent rotations.

The slot 150 extends helically along and about the tubular body 104 at a predetermined helical angle 155. The helical angle 155 is defined by the angle between the helix and the longitudinal direction y. In some examples, the helical angle 155 may range from about 5 degrees to about 85 degrees. In some preferred examples, the helical angle 155 may range from about 45 to about 85 degrees. In further preferred examples, the helical angle 155 may range from about 65 to about 85 degrees. The slot 150 may extend along the longitudinal direction y along the tubular body 104 helically in a clockwise or a counterclockwise helical direction.

The helical angle 155 may be selected based on the desired application of the shaft 100. The shaft 100 can have different degrees of flexibility along its length, and various desired flexibilities can be achieved by changing the helical angle 155. For example, in some specific uses, a shaft 100 being used in a medullary canal driver device, a suitable helix angle 155 may range from about 76 to about 82 degrees. More specifically, in situations where relatively low stiffness of the driver is desired, the helical angle 155 may be between about 80 and about 82 degrees. Where relatively high stiffness is desired, the helical angle 155 may be between about 76 degrees and about 78 degrees. When stiffness between the low and high stiffnesses is desired, the helical angle 155 may be between about 78 and about 80 degrees.

In some other specific uses, the shaft 100 may be used in a medullary canal reamer. More specifically, where relatively low stiffness is desired, the helical angle 155 may be between about 67 degrees and about 69 degrees. Where relatively high stiffness is desired, the helical angle 155 may be between about 63 degrees and about 65 degrees. Where stiffness is desired between the relatively low and high stiffnesses, the helical angle 155 may be between about 65 degrees and about 67 degrees. The rigidity of the shaft 100 can also be controlled through the design of the slot pattern, thereby enabling the use of thinner walls than would otherwise be require to produce equivalent rigidity.

Each rotation 168 includes a predetermined number of teeth 170, and each tooth 170 has predetermined dimensions. As described above, the size, shape, and quantity of teeth 170, as well as the helical angle 155 and the width of the slot 150, can affect the relative rigidity, flexibility, durability, and rotational strength of the shaft 100, and some or all of the above parameters may be varied to arrive the desired functional attributes of the shaft 100.

Figure 7:
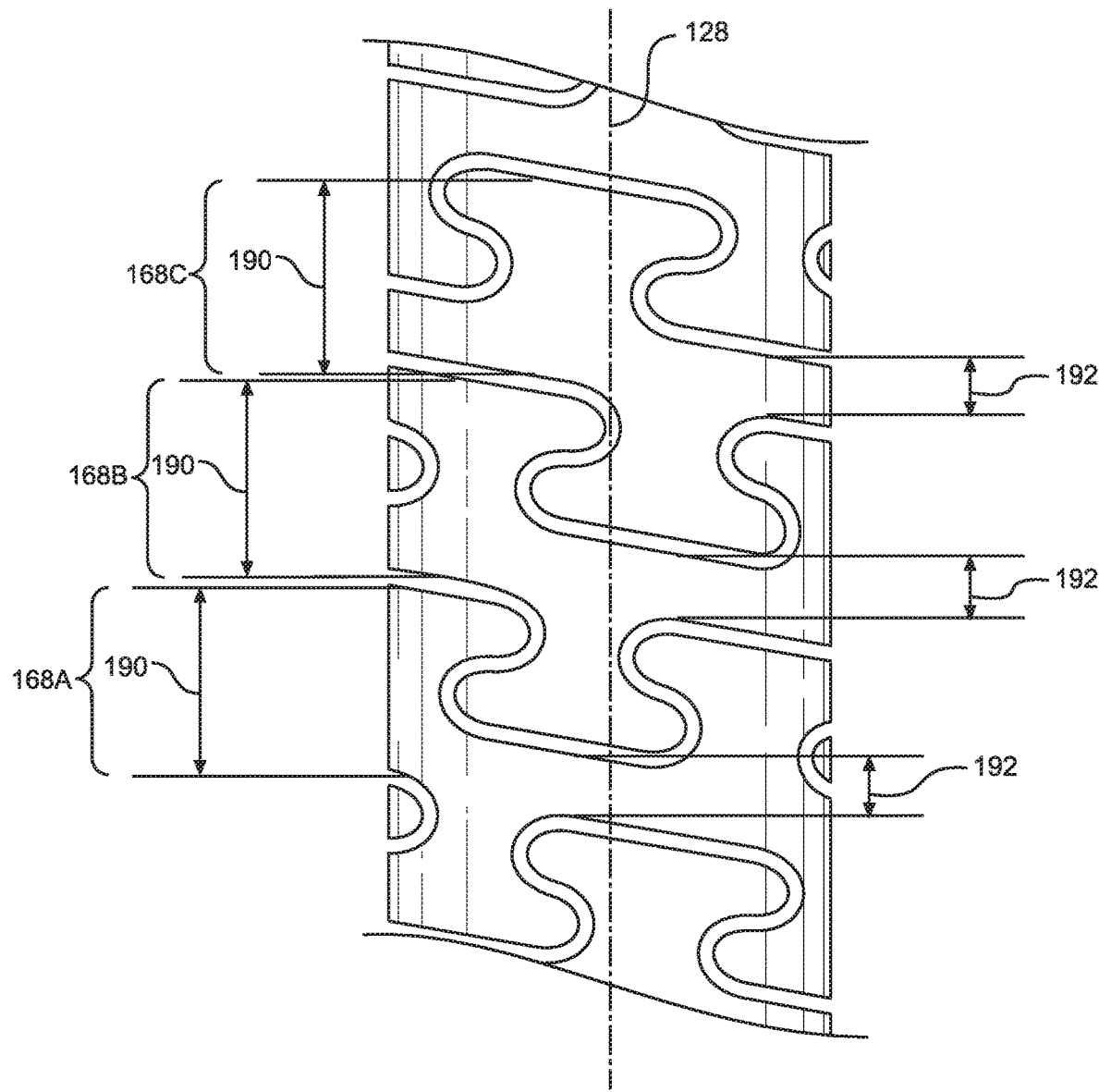
FIG. 7 illustrates a side perspective view of a portion of a flexible shaft according to an aspect of the disclosure.

The strength, durability, and ease-of-use of the shaft 100 may also depend on the arrangement of the sinusoidal pattern of the helical slot 150 and the teeth 170 defined by the sinusoidal pattern. Referring to FIG. 7, different distances between teeth 170 are depicted, with each distance being measured in a direction parallel to the central axis 128. Each distance is measured from the slot 150 of one rotation 168 to the slot 150 of the adjacent rotation 168. Each rotation 168 will have at least one maximum distance 190 and at least one minimum distance 192. The maximum distance 190 corresponds to the longest continuous portion of the tubular body 104 in the measured direction. The minimum distance 192 corresponds to the shortest continuous portion of the tubular body 104 in the measured direction. For purposes of this application, "continuous portion" means a portion of the tubular body 104 in the direction parallel to the central axis 128, the portion being uninterrupted by the slot 150. In some embodiments, a single rotation 168 may have a plurality of the same maximum distances 190 and/or a plurality of the same minimum distances 192.

The maximum distances 190 from at least two consecutive, adjacent rotations 168 are circumferentially offset from each other on the tubular body 104. Similarly, the minimum distances 192 from at least two consecutive, adjacent rotations 168 are circumferentially offset form each other on the tubular body 104. For example, FIG. 7 shows in detail three consecutive rotations 168: a first rotation 168*a*, a second rotation 168*b*, and a third rotation 168*c*. A maximum distance 190 is shown between each consecutive rotation 168. Similarly, a minimum distance 192 is shown between each consecutive rotation 168.

As shown in FIG. 7, the maximum distance 190 (measure in the longitudinal direction y) of the second rotation 168*b* is circumferentially offset, relative to the central axis 128, from the maximum distance 190 (also measured in the longitudinal direction y) of the first rotation 168*a*. Similarly, the minimum distance 192 (measured in the longitudinal direction y) of the second rotation 168*b* is circumferentially offset, relative to the central axis 128, from the minimum distance 192 (also measured in the longitudinal direction y) of the first rotation 168*a*. For illustrative purposes, it can be also seen that the maximum distance 190 and the minimum distance 192 of the third rotation 168*c* are also circumferentially offset from the maximum and minimum distances 190, 192, respectively, of both the first and second rotations 168*a*, 168*b*. Although three separate rotations 168 are depicted in FIG. 7, it will be understood that the number of consecutive rotations 168 having offset maximum and minimum distances 190, 192 may be a different number, for example, 2, 4, 5, 6, or another suitable number. In some embodiments, all rotations 168 of the helical sinusoidal slot 150 may have maximum and minimum distances 190, 192 that are circumferentially offset relative to the maximum and minimum distances 190, 192, respectively, of any other rotation 168 in the slot 150. A line extending through center points of features on teeth of at least two adjacent rotations of the helical path can be angularly offset from the central longitudinal axis.

Figure 8:
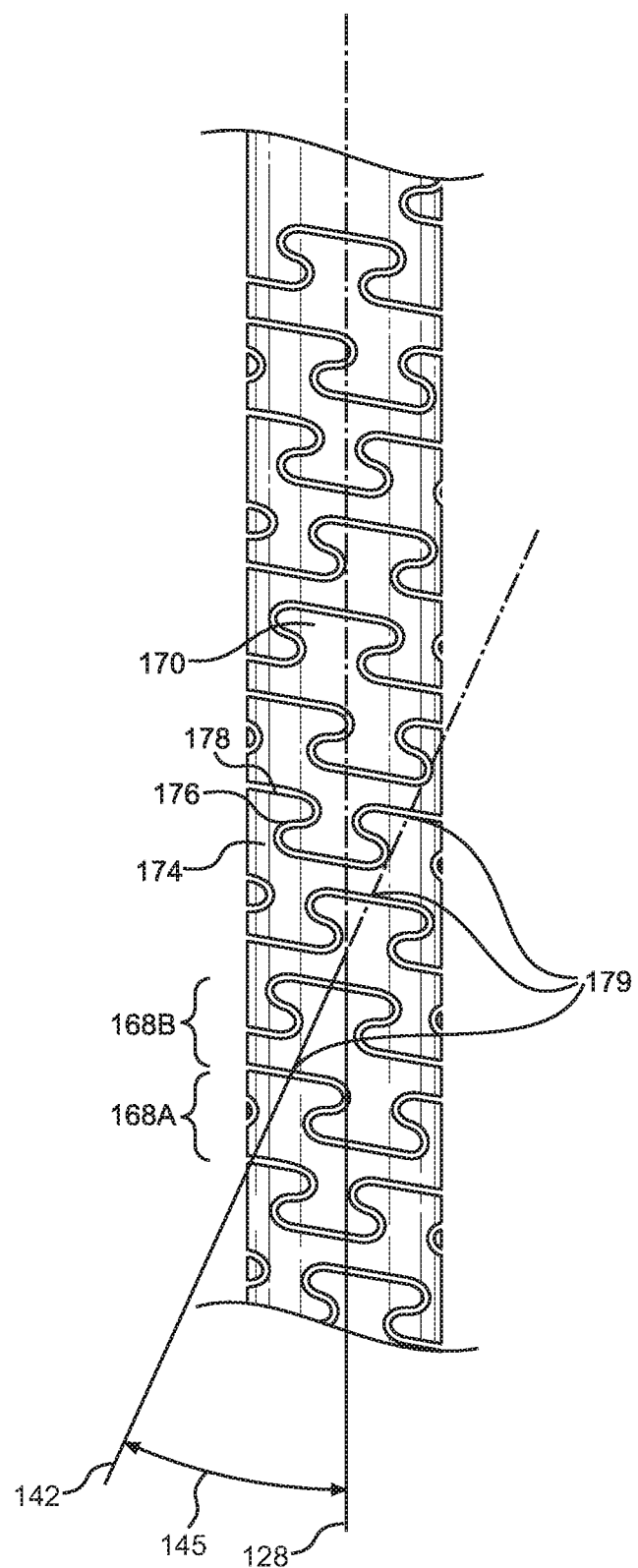
FIG. 8 illustrates a side perspective view of another portion of the flexible shaft of FIG. 7.

FIG. 8 depicts a reference line 142 shown passing through a plurality of teeth 170. The reference line 142 is shown passing through the same point of each tooth 170 (for example, through a center point 179 on the crown 178 of each tooth 170) and through teeth 170 that are in adjacent rotations 168 and are closest to one another along the longitudinal direction y. This depicted reference line 142 is not parallel to the central axis 128 and is angularly offset from the central axis 128. The reference line 142 may be offset from the central axis 128 at an offset angle 145. In some examples, the offset angle 145 may range from about 1 degree to about 90 degrees; from about 1 degrees to about 60 degrees; from about 1 degree to about 45 degrees; or in another suitable range. In some specific embodiments, the offset angle may be between about 6 degrees to about 38 degrees. The offset angle is measured from the longitudinal direction y. Although not depicted, it will be understood that a separate reference line may extend parallel to the reference line 142 and may pass through the plurality of teeth. If a line is drawn parallel to the central axis 128 of the embodiment of FIG. 8, such a line would intersect a different point on each feature of the teeth of at least two adjacent rotations of the helical path.

Figure 9:
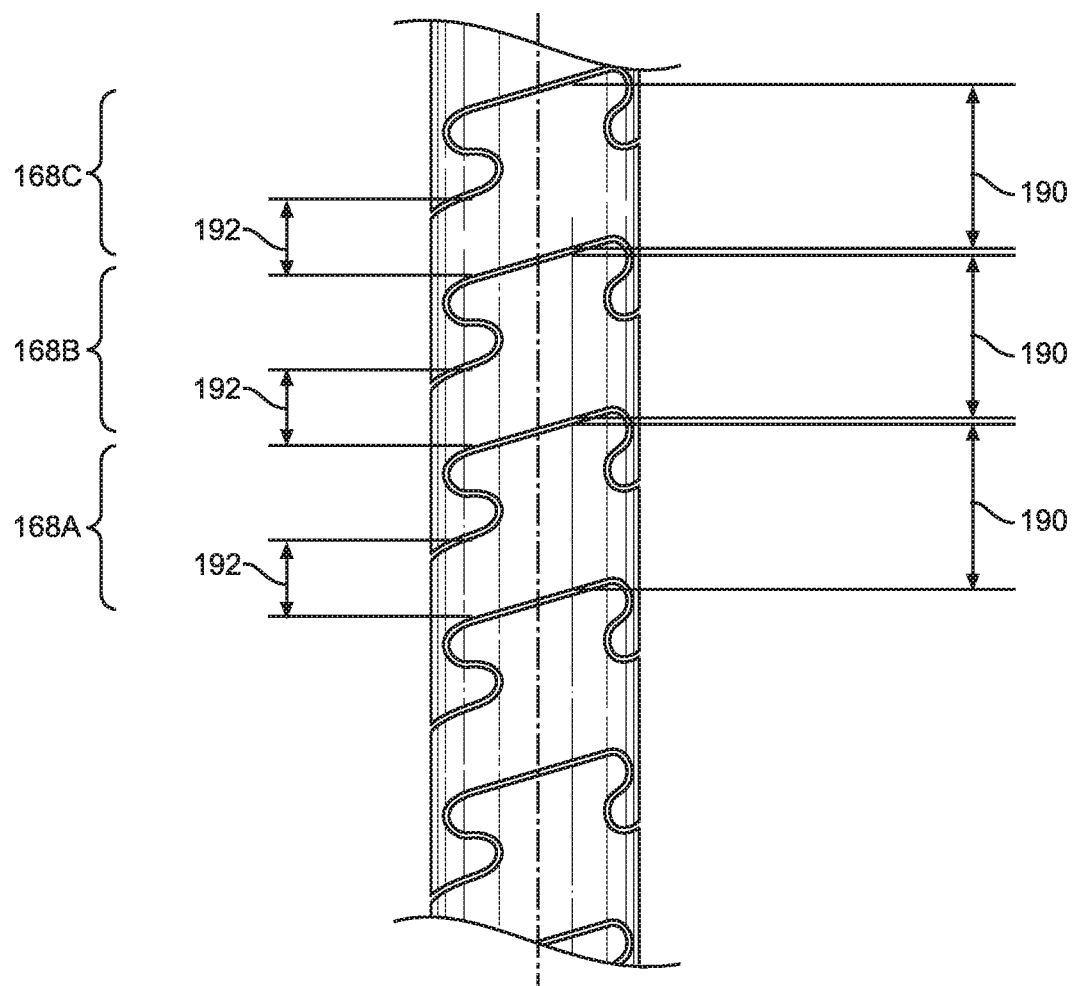
FIG. 9 illustrates a side perspective view of a portion of a flexible shaft that exists in the prior art.

By aligning consecutive adjacent maximum distances 190 (i.e. the "thick" pieces) and consecutive adjacent minimum distances 192 (i.e. the "thin" pieces) along reference lines that are angularly offset from the longitudinal direction y, the bending stiffness of the shaft 100 is better balanced along the length, thickness, and circumference of the shaft 100 than if the thick and thin pieces are aligned parallel to the longitudinal direction y. In existing devices (see, e.g., FIG. 9), teeth 170 are aligned along the longitudinal direction y such that the maximum distances 190 of adjacent consecutive rotations 168 are aligned parallel to the longitudinal direction y. Similarly, the minimum distances 192 of adjacent consecutive rotations 168 are also aligned parallel to the longitudinal direction y.

During rotation of the shaft 100, the bending stiffness of the shaft 100 fluctuations and varies to selectively increase or decrease. This results in vibrations of the shaft 100. This variation of bending stiffness may also result in variations in rotational speed of the shaft 100, as well as decrease the precision of torque being delivered along the shaft 100. Some or all of the above deficiencies can result in difficulty to align and position the shaft 100 in a desired orientation and location, as well as difficulty in maintaining the desired position and orientation of the shaft 100. Using such existing shafts can result in imprecise or inaccurate application of rotational force and torque to a target. In the embodiments disclosed herein, the "thick" and "thin" pieces of the shaft 100 are aligned such that the bending stiffness of the shaft 100 is balanced along the shaft 100 as the shaft 100 is rotated in either the first rotational direction 10*a* or the second rotational direction 10*b*.

Embodiments described throughout this application include components that may comprise various suitable materials. In some exemplary embodiments, the shaft 100 may be formed from stainless steel. In particular examples, the shaft 100 may include annealed stainless steel 304, 17-4 PH H900 stainless steel, 420 hardened stainless steel, 455 stainless steel H950, 465 H950 stainless steel, X15TN stainless steel, or another suitable stainless steel.

Figure 10:
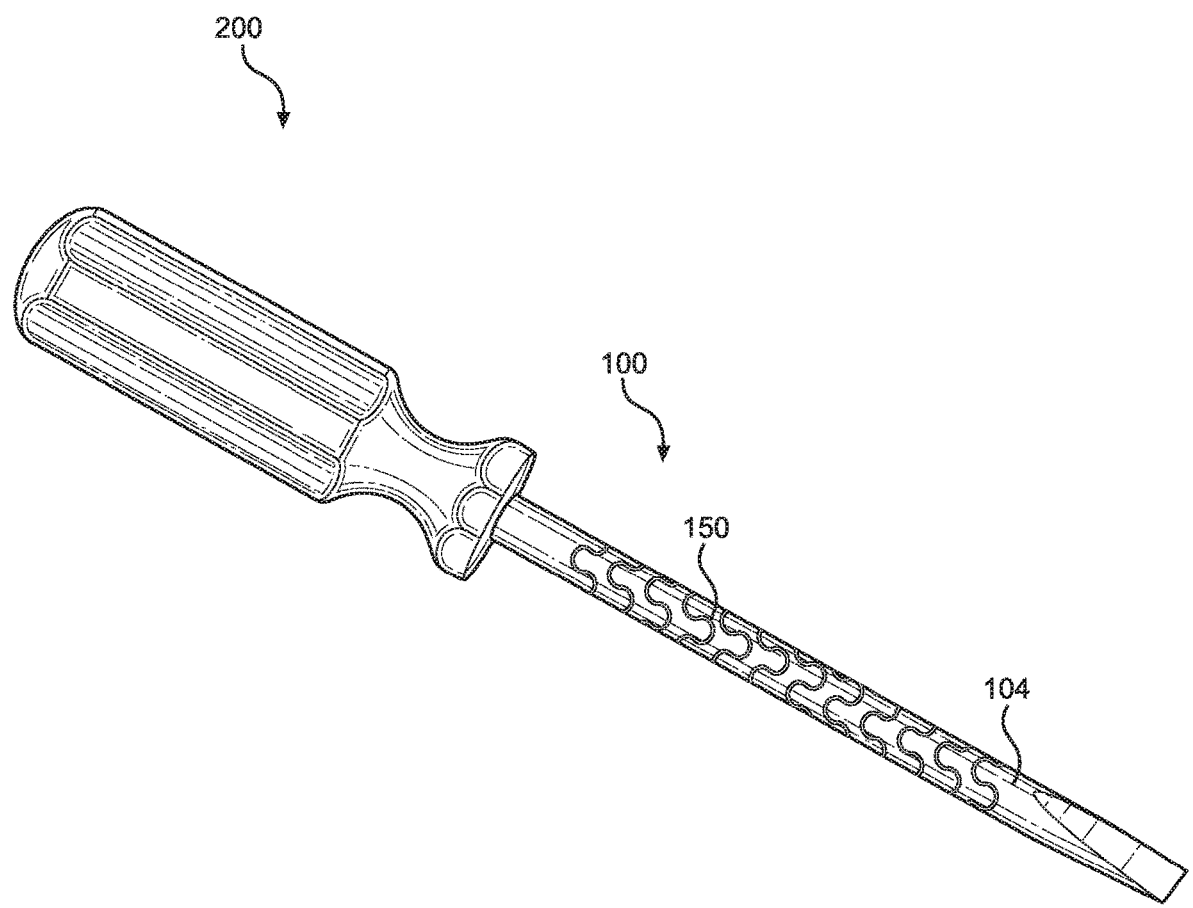
FIG. 10 illustrates a perspective view of a screwdriver with a flexible shaft according to another aspect of the disclosure.
Figure 11:
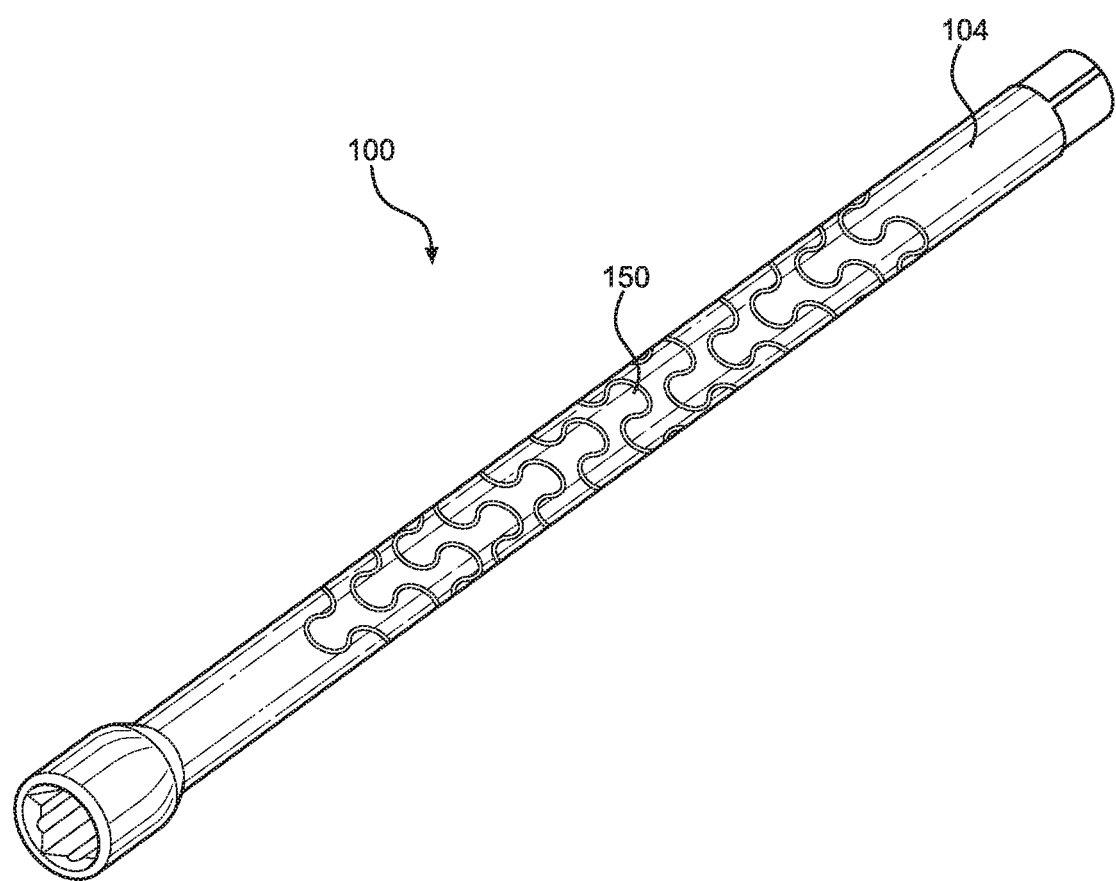
FIG. 11 illustrates a perspective view of a bit extender with a flexible shaft according to another aspect of the disclosure.
Figure 12:
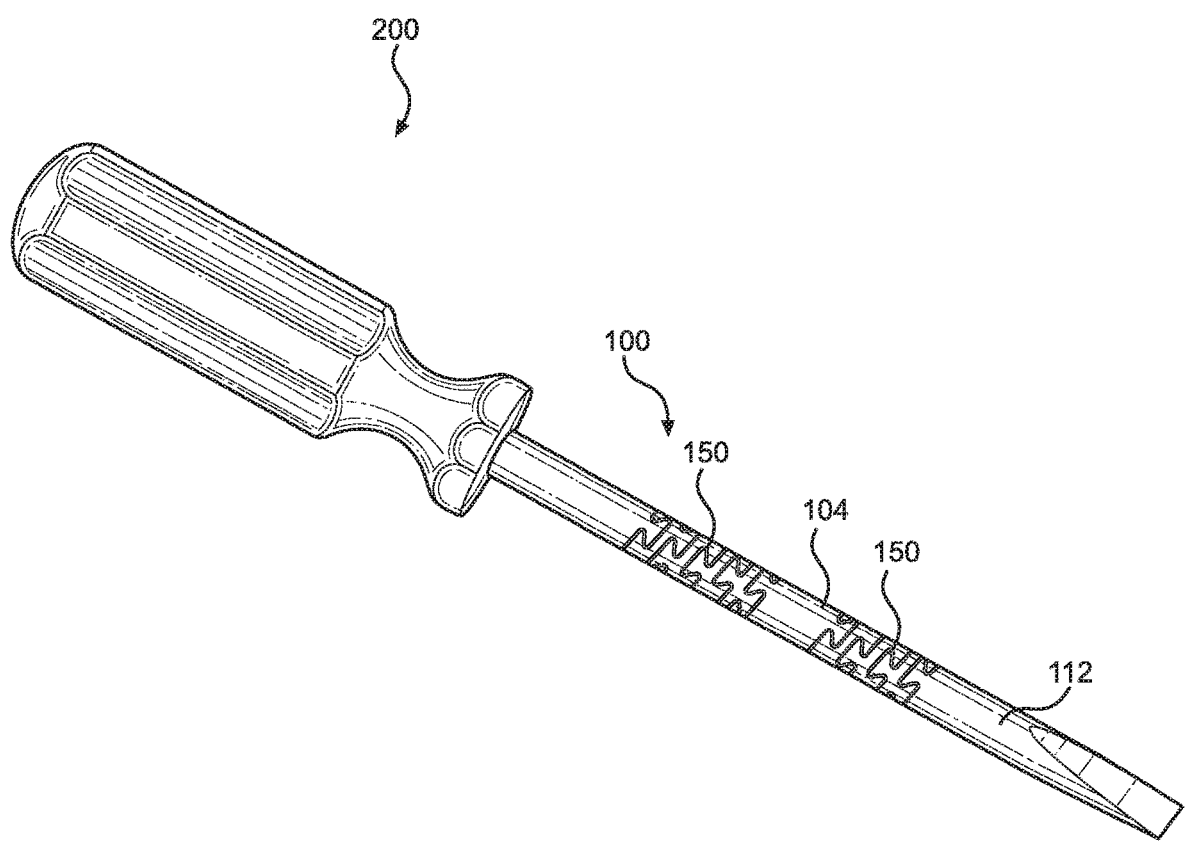
FIG. 12 illustrates a perspective view of a screwdriver with a flexible shaft having two slots according to yet another aspect of the disclosure.

Embodiments of shafts 100 depicted throughout this application are not limited to being used only in the screwdriver depicted in FIGS. 1 and 2. In some embodiments, the shaft 100 may be part of a bit extender (see FIG. 11). FIG. 10 depicts an alternative embodiment of a screwdriver 200 having a slot 150 that defines teeth 170 that have a curved crown 178 instead of a straight crown 178 shown in various other figures. FIG. 12 depicts an alternative embodiment of a screwdriver 200 having a shaft 100 that includes two slots 150 disposed on the same tubular body 104, each of the two slots 150 being arranged serially along the longitudinal direction y and being separate from one another by the tubular body 104.

While systems and methods have been described in connection with the various embodiments of the various figures, it will be appreciated by those skilled in the art that changes could be made to the embodiments without departing from the broad inventive concept thereof. It is understood, therefore, that this disclosure is not limited to the particular embodiments disclosed, and it is intended to cover modifications within the spirit and scope of the present disclosure as defined by the claims.

What is claimed is:

1. A flexible shaft, comprising:
   a tubular body extending along a central longitudinal axis, the tubular body having a proximal end and a distal end opposite the proximal end; and
   a slot defined by the tubular body and extending along a helical path around and along at least a portion of the tubular body between the proximal end and the distal end,
   wherein the helical path extends around the portion of the tubular body for a plurality of rotations,
   wherein the slot defines at least two teeth adjacent one another along a direction parallel to the central longitudinal axis, each tooth of the two teeth having a feature, and
   wherein a line extending through a center point of the feature on each of the two teeth is angularly offset from the central longitudinal axis.

2. The flexible shaft of claim 1, wherein the slot further defines a first tooth and a second tooth separated from the first tooth by the slot, and wherein the proximal end of the tubular body is configured to receive a rotational force about the central longitudinal axis in a first direction which causes the first tooth to contact the second tooth such that the rotational force is imparted from the first tooth to the second tooth.

3. The flexible shaft of claim 2, wherein the slot further defines a third tooth spaced from the second tooth, wherein the proximal end of the tubular body is configured to receive a rotational force in a second direction about the central longitudinal axis opposite the first direction which causes the third tooth to contact the second tooth such that the rotational force is imparted from the third tooth to the second tooth.

4. The flexible shaft of claim 1, wherein the slot is sinusoidal.

5. The flexible shaft of claim 1, wherein the two teeth are dovetail-shaped.

6. The flexible shaft of claim 1, wherein the flexible shaft is configured to bend about the central longitudinal axis.

7. The flexible shaft of claim 1, wherein the tubular body defines a lumen extending therethrough, the tubular body having an interior surface that defines the lumen and an exterior surface spaced radially from the interior surface in a direction orthogonal to the central longitudinal axis, and wherein the slot extends through the tubular body between the exterior surface to the interior surface.

8. The flexible shaft of claim 1, wherein the tubular body further defines a first stress relief opening adjacent a first end of the slot and a second stress relief opening adjacent a second end of the slot.

9. The flexible shaft of claim 8, wherein the first and second stress relief openings are circular openings.

10. The flexible shaft of claim 1, wherein the proximal end is configured to be removably coupled to a handle, a drill chuck, a screwdriver, a ratchet, or another flexible shaft.

11. The flexible shaft of claim 1, wherein the distal end is configured to be coupled to screwdriver tip, a drive bit, a reamer, or another rotating end effector.

12. The flexible shaft claim 1, wherein each tooth has a first side and a second side spaced from the first side, and wherein the feature of each tooth is a crown extending between the first and second sides.

13. The flexible shaft of claim 12, wherein the crown is flat or is curved.

14. The flexible shaft of claim 1, wherein the line is angularly offset from the central longitudinal axis by an angle between 1 degree and 90 degrees.

15. A flexible shaft, comprising:
    a tubular body extending along a central longitudinal axis, the tubular body having a proximal end and a distal end opposite the proximal end; and
    a slot defined by the tubular body and extending along a helical path around and along at least a portion of the tubular body between the proximal end and the distal end,
    wherein the helical path extends around the portion of the tubular body for a plurality of rotations,
    wherein the slot defines at least two teeth adjacent one another along a direction parallel to the central longitudinal axis, each tooth of the two teeth having a feature, and
    wherein a line parallel to the central longitudinal axis intersects a different point on each feature of the two teeth.

16. The flexible shaft of claim 15, wherein the slot further defines a first tooth and a second tooth separated from the first tooth by the slot, and wherein the proximal end of the tubular body is configured to receive a rotational force about the central longitudinal axis in a first direction which causes the first tooth to contact the second tooth such that the rotational force is imparted from the first tooth to the second tooth.

17. The flexible shaft of claim 16, wherein the slot further defines a third tooth spaced from the second tooth, wherein the proximal end of the tubular body is configured to receive a rotational force in a second direction about the central longitudinal axis opposite the first direction which causes the third tooth to contact the second tooth such that the rotational force is imparted from the third tooth to the second tooth.

18. The flexible shaft of claim 15, wherein the flexible shaft is configured to bend about the central longitudinal axis.

19. A modular flexible shaft comprising:
    a tubular body having a proximal end and a distal end opposite the proximal end, the tubular body extending along a central longitudinal axis between the proximal end and the distal end; and
    a slot extending along a helical path around and along at least a portion of the tubular body between the proximal end and the distal end; and a modular connection disposed on the distal end, the modular connection being configured to releasably couple to a modular component, wherein the helical path extends around the portion of the tubular body for a plurality of rotations, wherein the slot defines at least two teeth adjacent one another along a direction parallel to the central longitudinal axis, each tooth of the two teeth having a feature, and wherein a line extending through a center point of the feature on each of the two teeth is angularly offset from the central longitudinal axis.

20. The modular flexible shaft of claim 19, wherein the modular connection includes a screwdriver tip, a drive bit, a reamer, or another rotating end effector.

* * * * *